United States Patent [19]

Symon

[11] 4,140,718
[45] Feb. 20, 1979

[54] PREPARATION OF N,N'-DIALKYLPHENYLENEDIAMINES

[75] Inventor: Ted Symon, Lombard, Ill.

[73] Assignee: UOP Inc., Des Plaines, Ill.

[21] Appl. No.: 844,677

[22] Filed: Oct. 25, 1977

Related U.S. Application Data

[63] Continuation-in-part of Ser. No. 732,698, Oct. 14, 1976, abandoned.

[51] Int. Cl.$^2$ .................... C07C 85/08; C07C 85/11
[52] U.S. Cl. .................... 260/576; 260/577; 260/689
[58] Field of Search ............. 260/576, 577, 581, 582

[56] References Cited

U.S. PATENT DOCUMENTS

| | | | |
|---|---|---|---|
| 2,969,394 | 1/1961 | Chenicek | 260/577 |
| 3,336,386 | 8/1967 | Dovell et al. | 260/576 |
| 3,509,213 | 4/1970 | Greenfield et al. | 260/577 X |
| 3,522,309 | 7/1970 | Kirby | 260/577 |
| 3,978,040 | 8/1976 | Gottschlich et al. | 260/205 |
| 4,009,205 | 2/1977 | Kimura et al. | 260/577 X |

FOREIGN PATENT DOCUMENTS

862797 2/1971 Canada .................................. 260/577

OTHER PUBLICATIONS

CRC, "Handbook of Chemistry and Physics", 52nd Edition, p. C-111, 1971–1972.

*Primary Examiner*—Winston A. Douglas
*Assistant Examiner*—John Doll
*Attorney, Agent, or Firm*—James R. Hoatson, Jr.; Raymond H. Nelson; William H. Page, II

[57] ABSTRACT

N,N'-dialkylphenylenediamines are prepared by the reductive alkylation of a nitroaniline and a ketone in the presence of hydrogen and a hydrogenation catalyst. The desired product may be obtained in a more economical way when effecting the process in a continuous manner by utilizing an organic solvent comprising an ether compound such as a monoether of a dihydric alcohol, a diether of a dihydric alcohol, or a cyclic diether.

11 Claims, No Drawings

PREPARATION OF N,N'-DIALKYLPHENYLENEDIAMINES

CROSS-REFERENCE TO RELATED APPLICATIONS

This application is a continuation-in-part of my copending application Ser. No. 732,698 filed Oct. 14, 1976, now abandoned all teachings of which are incorporated herein by reference thereto.

BACKGROUND OF THE INVENTION

N,N'-dialkylphenylenediamines which are prepared by the reductive alkylation of a nitroaniline and a ketone in the presence of hydrogen and a suitable hydrogenation catalyst are utilized as additives for petroleum products such as gasoline in which the compounds act as an antioxidant and an inhibitor sweetening agent. The reaction for preparing the desired diamines may be effected under high pressure when utilizing either a batch or continuous type of operation. For example, when utilizing a batch type process the solid nitroaniline such as p-nitroaniline is poured into the reactor along with the catalyst, following which the ketone and the solvent are then added, the reactor is sealed, pressured with hydrogen, and heated to the desired operating temperature while subjecting the mixture to continuous agitation such as by stirring. The resultant product, which may comprise either a liquid or a low melting solid, is filtered free from the catalyst following which the solvent may then be removed by distillation.

When effecting the reductive alkylation process in a continuous manner, the reactants must, of necessity, be in solution in order that they may be continuously pumped into a reactor containing the catalyst and heated under hydrogen pressure. However, some difficulty is encountered when utilizing a continuous process inasmuch as p-nitroaniline has a poor solubility in most organic solvents. For example, it is almost insoluble in aliphatic hydrocarbons, only slightly soluble in aromatic hydrocarbons, and has a limited solubility in esters, alcohols and ketones. When utilizing a high molecular weight ketone as the alkylating agent, it has been found that excess ketone must be used as both the alkylating agent and solvent. However, the ketones which are used possess a particular disadvantage of being reduced to the corresponding alcohols and therefore it is necessary to dehydrogenate the alcohols back to the ketone. Likewise, when using low molecular weight ketones as alkylating agents, the ketones cannot be used in excess as a solvent due to the fact that they possess the facility of replacing both amine hydrogens of an aromatic amine, thereby forming undesirable overalkylated products such as trialkylated and tetraalkylated compounds.

The preparation of N,N'-diisopropyl-p-phenylenediamine, a particularly effective gasoline antioxidant and inhibitor sweetening agent, may be ued as an illustration of the problems which are encountered when preparing an N,N'-dialkyl-p-phenylenediamine. This compound is prepared by the reductive alkylation of p-nitroaniline with acetone. Inasmuch as, as hereinbefore set forth, p-nitroaniline as limited solubility in ketones, it is necessary to use an 8:1 mole ratio of acetone to p-nitroaniline in order to obtain a solution in which the p-nitroaniline is sufficiently solubilized so that the solution is capable of being pumped into a continuous plant. However, stoichiometrically, only a 2:1 mole ratio is required. The use of such an excess of acetone will cause further reaction with the dialkyl product to form unacceptable amounts of tri-N-alkylated by-products and will result in the loss of both acetone and hydrogen in the reduction of acetone to alcohol. In addition, the excess acetone will also interfere with the separation of water in the solvent recovery system of the plant.

Some prior art references have shown reductive alkylation processes. For example, Canadian Patent No. 862,797 discloses a reductive alkylation process in which a sulfided platinum catalyst is used for the reductive alkylation of an organic compound containing an amino and/or a nitro substituent. Likewise, U.S. Pat. No. 2,969,394 relates to a novel combination process which includes the reductive alkylation of an aromatic amino or nitro compound with a ketone during which an alcohol is formed from the ketone and converted back to the ketone for further use within the process. The patent describes an integrated continuous process for the manufacture of N,N'-di-sec-butyl-p-phenylenediamine in which the by-product, namely, 2-butanol, which results from the reduction of an excess of methyl ethyl ketone, which is employed to dissolve the p-nitroaniline, is isolated and converted back to the ketone for recycle. As will be hereinafter shown in greater detail, in the process of the present invention the use of excess ketone is avoided by solubilizing the nitroaniline in a solvent of the type set forth and therefore utilizing only enough ketone to satisfy the stoichiometry of the reductive alkylation reaction.

Another prior art patent, namely, U.S. Pat. No. 3,522,309 teaches the use of polar solvents such as a 5-20% amount of lower alcohols or hydrogenated hydrocarbons to increase the rate of the reductive alkylation reaction. However, the solvents which were utilized in this reference are not particularly effective as solvents for the nitroanilines.

As hereinafter set forth in greater detail, it has now been discovered that by utilizing certain organic solvents of the ether type it is possible to reductively alkylate a nitroaniline with ketones, and particularly low molecular weight ketones, in which the alkylating agent is present in a relatively low mole ratio, the ethers acting as a solvent for the nitroanilines.

SPECIFICATION

The invention relates to a process for the reductive alkylation of nitroanilines with a ketone. More specifically, the invention is concerned with an improvement in the reductive alkylation process for preparing N,N'-diaklylphenylenediamines whereby said process may be effected using relatively low mole ratios of alkylating agent to nitroaniline.

As hereinbefore set forth the product of the process of the present invention, namely, N,N'-dialkylphenylenediamines may be utilized as additives for petroleum products such as gasoline, fuel oil, jet fuel, heating oil, etc., whereby oxidation of the petroleum product with the corresponding formation of undesired gums and tars will be prevented or retarded. In addition, these compounds will also act as inhibitor sweetening agents.

It is therefore an object of this invention to provide an improved process for the preparation of N,N'-dialkylphenylenediamines.

A further object of this invention is to provide an improvement in the process for the reductive alkylation of a nitroaniline with a ketone utilizing a solvent which possesses a particular configuration.

In one aspect an embodiment of this invention resides in a process for the preparation of an N,N'-dialkyl-phenylenediamine which consists in the reductive alkylation of a nitroaniline and a ketone in the presence of hydrogen and a hydrogenation catalyst at reaction conditions and recovering the resultant N,N'-dialkyl-phenylenediamine, the improvement which consists in effecting said process in the presence of an organic solvent comprising an ether selected from the group consisting of the monoethers of dihydric alcohols, the diethers of dihydric alcohols and cyclic diethers.

A specific embodiment of this invention is found in a process for prepearing an N,N'-dialkyl-p-phenylenediamine which comprises reductively alkylating p-nitroaniline with acetone in the presence of hydrogen and a hydrogenation catalyst at a temperature in the range of from about 80° to about 240° C. and a pressure in the range of from about 2 to about 2000 pounds per square inch (psi), said process being effected in the presence of an organic solvent comprising 2-methoxyethanol.

Other objects and embodiments will be found in the following further detailed description of the present invention.

As hereinbefore set forth the present invention is concerned with an improvement in a process for the reductive alkylation of nitroanilines with a ketone, the improvement which comprises utilizing a particular type of solvent for the nitroaniline thereby permitting the reaction to be effected in the presence of a lesser amount of ketone. One advantage of utilizing this particular type of solvent for the reductive alkylation reaction is that p-nitroaniline is sufficiently soluble in the ethers so as to provide an economical plant throughput. In addition, the rate of reaction will be favorably increased as well as the amount of ketone which is utilized in the reaction can be reduced to slightly over the stoichiometric amounts, thus avoiding the formation of large quantities of alcohols with a concomitant dehydrogenation to form the desired ketone again. Furthermore, by utilizing the near stoichiometric amounts of ketones, it is possible to prevent the formation of overalkylated by-products, especially in reactions where low molecular weight ketones such as acetone, methyl ethyl ketone, cyclohexanone, etc., are employed. Examples of ether compounds which may be employed as solvents for the reaction of the present invention will include monoethers of dihydric alcohols, diethers of dihydric alcohols, and cyclic diethers. Some representative examples of these ethers which may be employed will include monoethers of dihydric alcohols such as 2-methoxyethanol, 2-ethoxyethanol, 2-propoxyethanol, 1-methoxy-2-propanol, 1-ethoxy-2-propanol, 1-propoxy-2-propanol, 1-methoxy-2-butanol, 1-ethoxy-2-butanol, 1-propoxy-2-butanol, etc.; the diethers of dihydric alcohols such as ethyleneglycol dimethyl ether, ethyleneglycol diethyl ether, ethyleneglycol dipropyl ether, diethyleneglycol dimethyl ether, diethyleneglycol diethyl ether, diethyleneglycol dipropyl ether, propyleneglycol dimethyl ether, propyleneglycol diethyl ether, propyleneglycol dipropyl ether, dipropyleneglycol dimethyl ether, dipropyleneglycol diethyl ether, dipropyleneglycol dipropyl ether, etc.; cyclic ethers such as 1,3-dioxane, 1,4-dioxane, etc. It is to be understood that the aforementioned ethers are only representative of the class of compounds which may be employed as solvents and that the present invention is not necessarily limited thereto.

The reductive alkylation of a nitroaniline with a ketone is effected by charging the nitroaniline such as o-nitroaniline or p-nitroaniline along with a ketone and the solvent to an appropriate apparatus along with the hydrogenation catalyst. The hydrogenation catalyst which is employed in the reductive alkylation can be chosen from any of those well known in the art such as nickel, platinum composited on a solid support such as alumina, palladium composited on alumina, or any other solid support such as carbon, diatomaceous earths, etc. The apparatus is sealed and pressured to the desired operating pressure with hydrogen, said pressure ranging from about 2 to about 2000 psi. Following this, the reaction mixture is thoroughly admixed by mechanical means such as stirrers and heated to the desired operating temperature which is in a range of from about 80° to about 240° C. Inasmuch as the reaction is exothermic in nature, due to the rapid reduction of the nitro groups, hydrogen will be rapidly consumed. Therefore it is necessary to maintain the desired operating pressure by an additional amount of hydrogen. At the end of the predetermined residence time, heating may be discontinued and the reaction mixture recovered from the apparatus after the apparatus has been returned to room temperature and the excess pressure vented. The desired product comprising an N,N'-dialkylphenylenediamine is separated from any unreacted starting materials and by-products by conventional means such as washing, drying, fractional distillation, etc., and recovered.

Examples of ketones which may be employed as alkylating agents in the reductive alkylation process of the present invention will include aliphatic ketones such as acetone, methyl ethyl ketone, diethyl ketone, methyl propyl ketone, methyl butyl ketone, methyl amyl ketone, methyl hexyl ketone, methyl heptyl ketone, methyl octyl ketone, methyl decyl ketone, ethyl propyl ketone, ethyl butyl ketone, ethyl amyl ketone, ethyl hexyl ketone, ethyl heptyl ketone, ethyl octyl ketone, ethyl nonyl ketone, dipropyl ketone, propyl butyl ketone, propyl amyl ketone, propyl hexyl ketone, propyl heptyl ketone, dibutyl ketone, the alkyl chains being either straight or branched chained in configuration, etc.; cycloaliphatic ketones such a cyclobutanone, cyclopentanone, cyclohexanone, cycloheptanone, cyclooctanone, etc.

It is also contemplated within the scope of this invention that the N,N'-dialkylphenylenediamine may also be prepared in a continuous manner of operation. When this type of operation is employed, the reactants comprising the nitroaniline dissolved in an appropriate solvent of the type hereinbefore set forth in greater detail and the ketone are continuously charged to a reactor which is maintained at the proper operating conditions of temperature and pressure and which contains a hydrogenation catalyst. In addition, hydrogen is also continuously charged to the vessel. Upon completion of the desired residence time in the reactor, the effluent is continuously withdrawn and subjected to conventional means of separation whereby the N,N'-dialkylphenylenediamine is separated from any unreacted starting materials and recovered, the unreacted starting materials being recycled to the reactor to form a portion of the feed stock.

Examples of N,N'-dialkylphenylenediamines which may be prepared according to the process of this invention will include N,N'-diisopropyl-p-phenylenediamine, N,N'-di-sec-butyl-p-phenylenediamine, N,N'-di-sec-amyl-p-phenylenediamine, N,N'-di-sec-hexyl-p-phenylenediamine, N,N'-di-sec-heptyl-p-phenylenediamine, N,N'-di-sec-octyl-p-phenylenediamine, N,N'-di-sec-nonyl-p-phenylenediamine, N,N'-di-sec-decyl-p-phenylenediamine, N,N'-dicyclopentyl-p-phenylenediamine, N,N'-dicyclohexyl-p-phenylenediamine, N,N'-dicycloheptyl-p-phenylenediamine, N,N'-diisopropyl-o-phenylenediamine, N,N'-di-sec-butyl-o-phenylenediamine, N,N'-di-sec-amyl-o-phenylenediamine, N,N'-di-sec-hexyl-o-phenylenediamine, N,N'-di-sec-heptyl-o-phenylenediamine, N,N'-di-sec-octyl-o-phenylenediamine, N,N'-di-sec-nonyl-o-phenylenediamine, N,N'-di-sec-decyl-o-phenylenediamine, N,N'-dicyclopentyl-o-phenylenediamine, N,N'-dicyclohexyl-o-phenylenediamine, N,N'-dicycloheptyl-o-phenylenediamine, etc.

The following examples are given for purposes of illustrating the process of this invention utilizing solvents comprising ethers. However, it is to be understood that these examples are given merely for purposes of illustration and that the present invention is not necessarily limited thereto.

EXAMPLE I

A charge consisting of 55.2 grams (0.4 mole) of p-nitroaniline, 61.5 grams (1.06 mole) of acetone and 280 grams of 2-methoxyethanol was added to a magnetically stirred 1-liter, stainless steel autoclave equipped with a hydrogen charging system, a sampling di-leg, a heater, a thermocouple well, and a water cooling coil. The autoclave also contained 12.7 grams of a hydrogenation catalyst comprising platinum on alumina. The autoclave was charged with the starting materials, sealed, flushed with hydrogen and thereafter pressured to 900 pounds per square inch gauge (psig) with hydrogen. The mixture was stirred and heated to a temperature of 100° C. Generally, an exothermic reaction took place as the temperature increased, this reaction indicating a rapid reduction of the nitro groups. Hydrogen was replaced in increments in order to maintain a pressure of 900 psig. The reaction was effected for a period of 4.8 hours, samples of the mixture being removed periodically through a dip-leg and analyzed by means of gasliquid chromatography. This analysis indicated that at the end of the period the substituted p-phenylenediamines recovered consisted of 97% N,N'-diisopropyl-p-phenylenediamine with 2% of the triisopropyl product and 1% of the monoisopropyl product.

EXAMPLE II

In this example a charge consisting of 55.2 grams of p-nitroaniline, 61.5 grams of acetone and 280 grams of 1-methoxy-2-propanol was placed in an autoclave similar to nature to that set forth in Example I above, said autoclave also containing 12.7 grams of a platinum on alumina hydrogenation catalyst. As in the above example, the autoclave was sealed, flushed with hydrogen and thereafter pressured to 900 psig. Stirring was commenced and the reaction mixture was heated to a temperature of 100° C. The autoclave and contents thereof were maintained at this temperature for a period of 5 hours, hydrogen being periodically in order to maintain the desired operating pressure. Analysis of the product by means of gas-liquid chromatography indicated that there was a 97% production of N,N'-diisopropyl-p-phenylenediamine with a 1% production of the triisopropyl product and 2% of the monoisopropyl product also being prepared.

EXAMPLE III

In a manner similar to that set forth in the above examples, the reductive alkylation of p-nitroaniline with acetone was effected in the presence of 280 grams of tetrahydrofuran. The reaction was effected in the presence of a platinum on alumina hydrogenation catalyst at a temperature of 100° C., a hydrogen pressure of 900 psig for a period of 5.2 hours. The reductively alkylated product which was obtained in this experiment consisted of 93% of N,N'-diisopropyl-p-phenylenediamine, 1% of the triisopropyl product and 6% of the monoisopropyl product.

EXAMPLE IV

To illustrate the use of a diether of a dihydric alcohol, the above experiments were repeated utilizing 280 grams of diethyleneglycol dimethyl ether as the solvent. The reaction conditions employed as well as the charge stock were similar to those in the above examples, the reaction being effected for a period of 4.5 hours. At the end of the reaction time, analysis of the product by means of gas-liquid chromatography determined that there had been a 93% production of N,N'-diisopropyl-p-phenylenediamien, a 4% production of N,N,N'-triisopropyl-p-phenylenediamine, and a 2% production of N-isopropyl-p-phenylenediamine.

It is therefore noted from the above examples that by utilizing a solvent of the type hereinbefore set forth, that is, an ether compound, it is possible to effect the reductive alkylation of p-nitroaniline with acetone using only an amount of acetone which is slightly above the stoichiometric amount in order to obtain the desired N,N'-diisopropyl-p-phenylenediamine product. The ability of the solvent to dissolve th p-nitroaniline so that such a relatively small amount of acetone could be used was a contributing factor to the obtention of the desired dialkyl product.

In addition, the ability of these solvents to remove water from the reaction mixture was also a contributing factor to obtaining the desired product in a relatively easy method. For example, 2-methoxyethanol was found to be soluble in and forming a binary azeotrope with water which consists of 85% water and 15% 2-methoxyethanol. Likewise, the diethyleneglycol diethyl ether formed a binary azeotrope which consisted of 78% water and 22% ether, while the other two solvents showed a binary mixture consisting of 49% water and 51% 2-methoxy-2-propanol and 5% water and 95% tetrahydrofuran respectively.

EXAMPLE V

To illustrate the applicability of the present process in a continuous manner of operation, a charge stock consisting of 15.1% acetone, 68.9% 2-methoxyethanol and 16% p-nitroaniline, the acetone/p-nitroaniline mole ratio being 2.3:1, was charged to a high pressure tubular reactor which was heated by a jacket at a LHSV of 0.5. In this reactor which was maintained at a temperature of 125° C. and a hydrogen pressure of 1000 psig, the reaction was effected for a period of 4 hours. The effluent was withdrawn to a liquid/vapor separator, passed from this separator to a liquid level controller and from there to a receiver. The effluent was analyzed by means of a gas-liquid chromatograph and the product was found to consist of 96% of N,N'-diisopropyl-p- phenylenediamine and 4% of N,N,N'-triisopropyl-p-phenylenediamine.

When the above run was repeated for a second 4-hour period utilizing a temperature of 150° C., and a LHSV of 1.0, the product was analyzed and found to consist of 96% N,N'-diisopropyl-p-phenylenediamine, 3% N,N,N'-triisopropyl-p-phenylenediamine and 1% N-isopropyl-p-phenylenediamine. A third run was effected for an additional 4-hour period utilizing a temperature of 170° C., and a LHSV of 1.5. Analysis of the product which was recovered from this run disclosed that the dialkyl product was present in a 95% amount, the trialkyl product was present in a 3% amount and the monoalkyl product was present in a 2% amount.

EXAMPLE VI

In this example another series of runs was effected in a continuous manner in an apparatus similar to that set forth in Example V above. The feed stock in this series of runs consisted of 18.1% acetone, 65.6% 2-methoxyethanol and 16.3% of p-nitroaniline, the acetone/p-nitroaniline mole ratio being 2.7:1. In the first 4-hour period, the reaction was effected at a temperature of 125° C., and a hydrogen pressure of 1000 psig, the feed stock being charged to the reactor at a LHSV of 1.0. The product which was recovered was analyzed and found to consist of 96% N,N'-diisopropyl-p-phenylenediamine and 4% N,N,N'-triisopropyl-p-phenylenediamine.

When the run above was repeated using a temperature of 150° C., and a LHSV of 1.5, the product consisted of 94% of the dialkyl product and 6% of the trialkyl product. A third run which was effected for a period of 4 hours at a temperature of 175° C., and a LHSV of 2.0 resulted in a product distribution which comprised 94% N,N'-diisopropyl-p-phenylenediamine and 6% of the trialkylated product, namely, N,N,N'-triisopropyl-p-phenylenediamine.

EXAMPLE VII

In this example a charge consisting of 55.2 grams (0.4 mole) of o-nitroaniline, 61.5 grams (1.06 mole) of acetone, and 280 grams of 2-methoxyethanol may be added to a magnetically stirred stainless steel autoclave which is provided with a hydrogen charging system, a sampling dip-leg, a heater, a thermocouple well, and a water cooling coil. The catalyst which may be employed for this process comprises 12.7 grams of platinum on alumina. After charging the autoclave with the starting materials it may then be sealed, flushed with hydrogen, and pressured to about 1000 psig with hydrogen. Thereafter the mixture may be stirred and heated to a temperature of 100° C. being maintined for a period of about 5 hours while maintaining the pressure of 900 psig by the addition of incremental portions of hydrogen. At the end of the 5 hour period heating may be discontinued, the excess pressure discharged, and after return to room temperature the desired product comprising N,N'-diisopropyl-o-phenylenediamine may be recovered from the autoclave.

EXAMPLE VIII

The use of other ketones such as methyl ethyl ketone, diethyl ketone and cyclohexanone which are relatively low molecular weight compounds as alkylating agents in the reductive alkylation of o-nitroaniline or p-nitroaniline using solvents of the type hereinbefore set forth may permit the use of slightly over stoichiometric amounts of the ketones due to the ability of these solvents to dissolve the nitroanilines.

I claim as my invention:

1. In a process for the preparation of an N,N'-dialkylphenylenediamine which consists in the reductive alkylation of a nitroaniline and a ketone in the presence of hydrogen and a hydrogenation catalyst at reaction conditions and recovering the resultant N,N'-dialkylphenylenediamine, the improvement which consists in effecting said process in the presence of an organic solvent comprising an ether selected from a group consisting of the monoethers of dihydric alcohols, the diethers of dihydric alcohols, and cyclic diethers.

2. The process as set forth in claim 1 in which said reaction conditions include a temperature in the range of from about 80° to about 240° C., and a pressure in the range of from about 2 to about 2000 pounds per square inch.

3. The process as set forth in claim 1 in which said ketone is acetone.

4. The process as set forth in claim 1 in which said ketone is methyl ethyl ketone.

5. The process as set forth in claim 1 in which said ketone is diethyl ketone.

6. The process as set forth in claim 1 in which said ketone is cyclohexanone.

7. The process as set forth in claim 1 in which said monoether of a dihydric alcohol is 2-methoxyethanol.

8. The process as set forth in claim 1 in which said monoether is 1-methoxy-2-propanol.

9. The process as set forth in claim 1 in which said diether of a dihydric alcohol is diethyleneglycol dimethyl ether.

10. The process as set forth in claim 1 in which said nitroaniline is p-nitroaniline.

11. The process as set forth in claim 1 in which said nitroaniline is o-nitroaniline.

* * * * *